United States Patent [19]

Tanaka et al.

[11] Patent Number: 4,891,453

[45] Date of Patent: Jan. 2, 1990

[54] PROCESS FOR PRODUCING P,P'-BIPHENOL

[75] Inventors: Michio Tanaka; Yoshito Kurano; Katsuo Taniguchi, all of Iwakuni; Masayasu Ishibashi, Kuga, all of Japan

[73] Assignee: Mitsui Petrochemical Industries, Ltd., Tokyo, Japan

[21] Appl. No.: 247,333

[22] Filed: Sep. 21, 1988

[30] Foreign Application Priority Data

Sep. 22, 1987 [JP] Japan .................................. 62-238230
Sep. 30, 1987 [JP] Japan .................................. 62-246317
Oct. 15, 1987 [JP] Japan .................................. 62-261272
Nov. 2, 1987 [JP] Japan .................................. 62-278102

[51] Int. Cl.$^4$ ........................ C07C 37/50; C07C 39/12
[52] U.S. Cl. ...................................... 568/805; 568/730
[58] Field of Search ................................ 568/730, 805

[56] References Cited

U.S. PATENT DOCUMENTS 4,205,187 5/1980 Cardenas et al. .................... 568/805

Primary Examiner—Werren B. Lone
Attorney, Agent, or Firm—Nixon & Vanderhye

[57] ABSTRACT

A process is disclosed which is capable of producing p,p'-biphenol of high purity by the dealkylation reaction of 3,3',5,5'-tetra-t-butyl-4,4'-dihydroxybiphenyl and which yet allows isobutene to be recovered in high yield. The process performs the dealkylation reaction of 3,3',5,5'-tetra-t-butyl-4,4'-dihydroxybiphenyl in the presence of an acid catalyst using as a solvent a saturated hydrocarbon having a boiling point of 190° C. or above, an alicyclic hydrocarbon having a boiling point of 190° C. or above, a hydrocarbon with an iodine value of no more than 1, sulfolane, or a mixture of these solvents. Also disclosed is a process for producing p,p'-biphenol from a mixture of 2,6-di-t-butyl-phenol and 3,3',5,5'-tetra-t-butyl-4,4'-diphenoquinone or from a mixture of 2,6-di-t-butylphenol, 3,3',5,5'-tetra-t-butyl-4,4'-diphenoquinone and 3,3',5,5'-tetra-t-butyl-4,4'-dihydroxybiphenyl. In this process, the synthesis of 3,3',5,5'-tetra-t-butyl-4,4'-dihydroxybiphenyl by the redox reaction between 2,6-di-t-butylphenol and 3,3',5,5'-tetra-t-butyl-4,4'-diphenoquinone and the production of p,p'-biphenol by the dealkylation reaction of 3,3',5,5'-tetra-t-butyl-4,4'-dihydroxybiphenyl are performed at one stage in the presence of both an acid catalyst and a solvent at a temperature of 120°–280° C.

5 Claims, No Drawings

PROCESS FOR PRODUCING P,P'-BIPHENOL

BACKGROUND OF THE INVENTION

The present invention relates to a process for producing p,p'-biphenol. More particularly, the present invention relates to a process for producing p,p'-biphenol by dealkylating 3,3',5,5'-tetra-t-butyl-4,4'-dihydroxybiphenyl.

It is known that when phenols, in particular alkyl-substituted phenols, are oxidized under certain conditions, biphenols and dipheno-quinone compounds are produced by an oxidative coupling reaction. Among the products obtained, p,p'-biphenol is useful as the starting material for the synthesis of polyesters or polycarbonates, as an intermediate for the production of dyes, pharmaceuticals and agri-chemicals, as the starting material for the production of liquid-crystal polymers, or as a photographic agent. Because of this great variety of applications in which p,p'-biphenol finds its potential use, this compound has drawn much attention from researchers in various fields of industry.

When 3,3',5,5'-tetra-t-butyl-4,4'-dihidoxybiphenyl (hereinafter sometimes abbreviated as TTBP) is dealkylated in the presence of both a solvent and a catalyst to obtain p,p'-biphenol (which is hereinafter sometimes abbreviated as DHBP), isobutene is also produced as a by-product. This isobutene is also important for industrial purposes since it can be polymerized into isooctane and polymeric gasoline or can be used as a starting material for the production of butyl rubber by copolymerization of isoprene and isobutene.

While several methods have heretofore been proposed in the art of producing p,p'-biphenol from 3,3',5,5'-tetra-t-butyl-4,4'-biphenol (hereinafter sometimes abbreviated as TTBP), they all have their own problems as described below.

Japanese Pat. Application (OPI) No. 92332/1980 filed by UCC (the term OPI as used herein means an unexamined published Japanese patent application) discloses a process for producing p,p'-biphenol by debutylating TTBP in the absence of both a solvent and a catalyst but this method is not practical for industrial purposes since it requires temperatures of at least 300° C.

Japanese Pat. Application (OPI) No. 1434/1984 discloses a process for simultaneous production of p,p'-biphenol and meta-t-butylphenol by reacting TTBP and phenol under heating in the presence of an activated clay catalyst so that the t-butyl group of TTBP is transalkylated on meta-position of phenol. This method also is not practical for the purpose of industrial production of p,p'-biphenol from TTBP since the meta-t-butylphenol produced from TTBP together with p,p'-biphenol cannot be utilized effectively.

Japanese Pat. Publication No. 135/1987 discloses a method of producing DHBP by debutylation of TTBP using, as a solvent, diphenyl ether which may optionally contain the butylated diphenyl ether resulting from the debutylation of TTBP. Japanese Pat. Application (OPI) No. 189127/1983 discloses a process for producing p,p'-biphenol in which TTBP is debutylated at 120°-250° C. in the presence of catalyst sulfuric acid or sulfonic acid to produce p,p'-biphenol using, as a solvent, phenol which is optionally substituted by a lower alkyl or alkoxy group, and the resulting p,p'-biphenol is separated by filtration at a temperature between the melting point of the solvent and 80° C. However, in each of these methods, the isobutene resulting from the debutylation of TTBP will be added to the unsubstituted phenol or substituted phenols used as a solvent and this "transalkylation" causes t-butylphenol to be produced in large quantities.

Japanese Pat. Application (OPI) Nos. 23338/1985 and 200935/1986 also disclose a method for producing p,p'-biphenol from TTBP using diphenyl ether as a solvent. But in this method part of the isobutene formed by the debutylation of TTBP is transalkylated on the solvent diphenyl ether to produce t-butyldiphenyl ethers, thereby reducing the recovery of isobutene.

If decane or other materials that have low miscibility with TTBP are used as solvents in the production of DHBP from TTBP, the product DHBP will adhere to the wall or the reaction vessel and give considerable difficulty in handling.

It has also been known that p,p'-biphenol can be produced from 2,6-di-t-butylphenol. The route of synthesis of p,p'-biphenol from 2,6-di-t-butylphenol is expressed by the following reaction schemes (1) and (2):

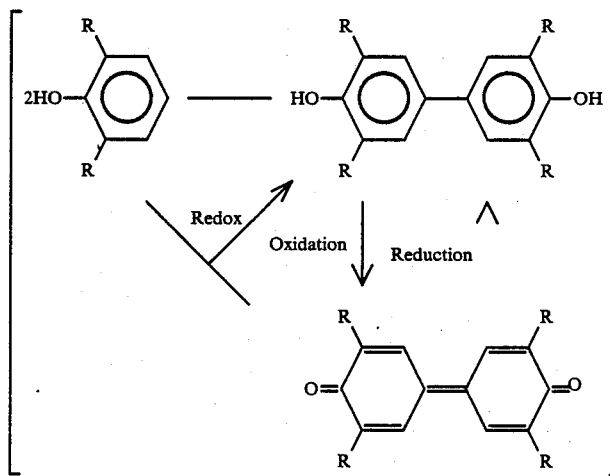

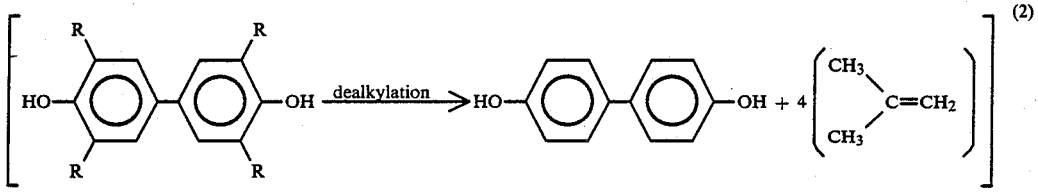

where R is a t-butyl group.

An example of the method of performing the first-stage reaction denoted by scheme (1) is disclosed in Japanese Pat. Application (OPI) No.72131/1980, which describes a process for producing 3,3′,5,5′-tetra-t-butyl-4,4-dihydroxybiphenyl from 2,6-di-t-butylphenol by performing this first-stage reaction under predetermined conditions in the presence of an alkali catalyst such as an alkali metal hydroxide. However, it is difficult to selectively obtain 3,3′,5,5′-tetra-t-butyl-4,4′-dihydroxybiphenyl in high yield by this process and the resulting 3,3′,5,5′-tetra-t-butyl-4,4′-dihydroxybiphenyl may be further oxidized to yield 3,3′,5,5′-tetra-t-butyl-4,4′-diphenoquinone as a by-product. This by-product 3,3′,5,5′-tetra-t-butyl-4,4′-diphenoquinone can be reduced to TTBP by treatment with a reducing agent such as hydrogen. But this reduction reaction is usually performed after the 3,3′,5,5′-tetra-t-butyl-4,4′-diphenoquinone has been isolated, so the overall manufacturing process will inevitably become complicated.

Japanese Pat. Application (OPI)No. 200935/1986 discloses a process for producing p,p′-biphenol which generally comprises: treating 2,6-di-t-butylphenol with oxygen or a like substance in the presence of a potassium hydroxide catalyst until 20–40% of the 2,6-di-t-butylphenol is converted to 3,3′,5,5′-tetra-t-butyl-4,4′-diphenoquinone; reacting the residual 2,6-di-t-butylphenol with 3,3′,5,5′-tetra-t-butyl-4,4′-diphenoquinone; distilling off the unreacted 2,6-di-t-butylphenol under vacuum and recovering the liquid bottoms chiefly composed of TTBP; dissolving the recovered liquid bottoms in a specified solvent; filtering off the potassium hydroxide catalyst; and debutylating the 3,3′,5,5′-tetra-t-butyl-4,4′-dihydroxybiphenyl in the filtrate in the presence of a catalyst.

However, this method has the problem that in order to remove the potassium hydroxide catalyst from the reaction solution, the liquid bottoms chiefly composed of 3,3′,5,5′-tetra-t-butyl-4,4′-dihydroxybiphenyl must be dissolved in a specified solvent such as diphenyl ether. As a further problem, the starting 2,6-di-t-butylphenol must be distilled off under vacuum in order to obtain the liquid bottoms. Because of these problems, the method still suffers a disadvantage in that it involves too complicated procedures to justify its application to commercial production of p,p′-biphenol.

As described above, p,p′-biphenol has been known to be capable of being produced from 2,6-di-t-butylphenol. Conventionally, the reaction expressed by scheme (1) is completed with proper conditions being selected with respect to such factors as catalyst, and thereafter TTBP is separated from the reaction mixture. Then, with another set of conditions including acid catalyst being selected, the second-stage reaction (dealkylation) expressed by scheme (2) is performed to produce p,p′-biphenol.

However, in order to produce p,p′-biphenol from 2,6-di-t-butylphenol by the method described above, TTBP must be separated from the mixture consisting 2,6-di-t-butylphenol, 3,3′,5,5′-tetra-t-butyl-4,4′-diphenoquinone and TTBP, and this adds to the complexitity of the overall process or p,p′-biphenol production.

SUMMARY OF THE INVENTION

An object, therefore, of the present invention is to solve the aforementioned problems of the prior art by providing a process for producing p,p′-biphenol which is capable of not only obtaining DHBP of high purity from TTBP but also recovering the concomitant isobutene in high yield.

Another object of the present invention is to provide a process for producing p,p′-biphenol which, in addition to the features described above, has a capability for permitting the spent solvent to be recycled for another use in the intended reaction.

In short, the first embodiment of the present invention provides the process for producing p,p′-biphenol by the dealkylation reaction of 3,3′,5,5′-tetra-t-butyl-4,4′-dihydroxybiphenyl, the reaction being carried out in the presence of an acid catalyst using as solvent a saturated hydrocarbon having a boiling point of 190° C. or above, an alicyclic hydrocarbon having a boiling point of 190° C. or above, a hydrocarbon with an iodine value of no more than 1, sulfolane, or a mixture of these solvents.

A further object of the present invention is to provide a process for producing p,p′-biphenol in which 2,6-di-t-butylphenol is reacted with 3,3′,5,5′-tetra-t-butyl-4,4′-diphenoquinone under predetermined conditions, or 2,6-di-t-butylphenol, 3,3′,5,5′-tetra-t-butyl-4,4′-diphenoquinone and 3,3′,5,5′-tetra-t-butyl-4,4′-dihydroxybiphenyl are reacted under predetermined conditions, thereby directly obtaining p,p′-biphenol in one step without separating 3,3′,5,5′-tetra-t-butyl-4,4′-dihydroxybiphenyl from the reaction product.

Still another object of the present invention is to provide a method for producing p,p′-biphenol by subjecting 2,6-di-t-butylphenol to reaction under predetermined conditions and which yet is simplified in the manufacturing process because of the absence of the need to separate any of the reaction intermediates of catalyst used.

DETAILED DESCRIPTION OF THE INVENTION

To start with, the first aspect of the present invention is described which relates to a process for producing p,p′-biphenol (DHBP) by dealkylation of 3,3′,5,5′-tetra-t-butyl-4,4′-dihydroxybiphenyl (TTBP).

The pathway of formation of p,p′-biphenol from the starting TTBP may be expressed by the following reaction scheme:

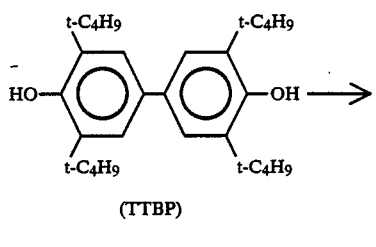

(TTBP)

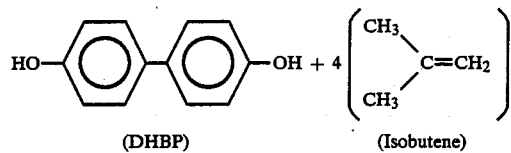

(DHBP)   (Isobutene)

In carrying out the reaction noted above, an acid such as sulfuric acid or sulfonic acid is used as a catalyst. Illustrative sulfonic acids include p-toluenesulfonic acid, perfluorosulfonic acid and methanesulfonic acid. Besides sulfuric acid and sulfonic acids, heteropolyacids may be used as catalysts. Useful heteropolyacids include phosphotungstic acid, phosphomolybdic acid and silicomolybdic acid. Other usable catalyst acids are Lewis acids such as aluminum chloride, aluminum isopropoxide and aluminum phenoxide. In certain cases, solid acids as well as liquid acids may be used. Illustrative solid acids include ion-exchange resins (e.g. Amberlist), mordenite, silica alumina, tetrasilicic mica, activated clay, zeolite, synthetic mica and clay minerals.

Solvents that can be used in the present invention include saturated hydrocarbons having boiling points of 190° C. and above, alicyclic hydrocarbons having boiling points of 190° C. and above, hydrocarbons having iodine values of not more than 1, sulfolane, and mixtures thereof. Illustrative saturated hydrocarbons having boiling points of 190° C. and above include paraffins such as tridecane, octadecane and eicosane, and paraffinic mixtures such as gas oil. A typical example of the alicyclic hydrocarbons having boiling points of 190° C. and above is decalin. Illustrative hydrocarbons having iodine values of no more than 1 are Lucant ® and ehylene-propylene oligomers having molecular weights of 200–2,000. Specific examples of Lucant ® that can be used in the present invention include: α-olefin homopolymers, cooligomers and ethylene/α-olefin cooligomers such as polydecene, polybutene, ethylene/propylene oligomer and isobutylene/n-butylene copolymer; and cycloalkanes such as 2,4-dicyclohexyl-2-methylpentane.

Among these examples, ethylene/α-olefin cooligomers are particularly preferred for use as solvents in the present invention. Specific examples of such oligomers are compounds represented by the following general formula:

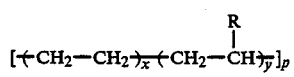

(where R is a hydrocarbon group denoted by $C_nH_{2n+1}$; and n, x, y and p each signifies an integer), with the ratio of x/y being normally in the range of 0.4–2.5. Cooligomers having the above-noted general formula and which can be used in the present invention may be classified by kinematic viscosity (cSt) as measured at 100° C. and are available at values of 5, 10, 20, 50, 100, 150, etc. The integers of x, y and p may be selected at any desired values so long as the kinematic viscosity is in the range specified above. Specific examples of R include methyl, ethyl, propyl and butyl groups.

Preferably, sulfolane (tetramethylene sulfone) is used as a solvent. The chemical formula of sulfolane is

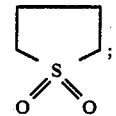

it has a melting point of 27.4°–27.8° C. and a boiling point of 285° C., and is readily soluble in water and acetone.

When liquid acid catalysts such as sulfuric acid and p-toluene-sulfonic acid are used, they remain liquid throughout the reaction. On the other hand, the product p,p'-biphenol has low solubility in the solvent, so it will precipitate as a crystal. Therefore, when liquid acid catalysts are used, the solvent and catalyst used in the present invention can be readily separated from p,p'-biphenol by standard operations such as filtration and centrifugation. In the case where solid acids such as silica alumina and activated clay are used, alcohols, ketones or other solvents that dissolve p,p'-biphenol are added to the reaction mixture after completion of the reaction, and the product, p,p'-biphenol in the resulting solution may be freed of the catalyst by routine steps such as filtration and centrifugation.

Thereafter, p,p'-biphenol dissolved in alcohols, ketones or other solvents that have high capability for dissolving p,p'-biphenol may be separated from the solvents by crystallization which is effected after all or part of the solvents has been distilled off. If desired, the solvents need not be distilled off before crystallization. Alcohols, ketones and other solvents that have high capability for dissolving p,p'-biphenol may be exemplified by methanol, ethanol, propanol, isopropyl alcohol, acetone, methyl isobutyl ketone, methyl ethyl ketone, dioxane, tetrahydrofuran and sulfolane.

The above-described reaction is preferably carried out under the following conditions, which are given here simply as a guide and may be varied as required. Speaking of the solvent, saturated hydrocarbons having boiling points of 190° C. and above, or alicyclic hydrocarbons having boiling points of 190° C. and above, or hydrocarbons having iodine values of no more than 1, or mixtures thereof are generally used in amounts ranging from 0.1 to 20 times, preferably from 1 to 5 times, the weight of TTBP used as the starting material. Sulfolane is generally used in amounts ranging from 0.5 to 20 times, preferably from 1 to 10 times, the weight of the starting TTBP.

Acids is catalysts are generally used in amounts ranging from 0.01 to 10 wt %, preferably from 0.05 to 5 wt %, of the starting TTBP.

Except in the case where sulfolane is used as a solvent, the reaction temperature is preferably within the range of 150°–300° C., with the range of 170°–280° C. being particularly preferred. If the reaction temperature exceeds 300° C., the decomposition of p,p'-biphenol and the formation of high-boiling point substances will occur, which certainly should be avoided. If the reaction temperature is less than 150° C., the rate of dealkylation reaction becomes too slow to be feasible for practical purposes. In the present invention, the reaction can be allowed to proceed at comparatively low temperatures (300° C.) which are feasible in commercial operations.

If sulfolane is used as a solvent, the reaction temperature is preferably within the range of 150°–285° C., with the range of 180°–250° C. being particularly preferred.

The reaction time varies greatly with the reaction temperature employed and is preferably in the range of 1 to 10 hours.

If solvents of the types described above are used in carrying out the reaction for producing p,p'-biphenol from TTBP, there is little possibility of the occurrence of "transalkylation" in which part of the isobutene that has formed as a result of de-t-butylation of TTBP is added to the solvent. This contributes to an improvement in the recovery of isobutene.

The use of sulfolane as a solvent for the reaction of forming DHBP from TTBP has a particular advantage over the case where phenol or substituted phenols, or diphenyl ether or butylated diphenyl ether is used as a solvent in that there is no possibility of t-butyl phenol or other unwanted products of being formed as a result of transalkylation with isobutene, or the t-butyl group eliminated from TTBP. This offers the advantage that isobutene can be recovered in high yield, with the solvent sulfolane being purified for further use in the reaction.

Sulfolane has a very high capability for dissolving DHBP which is the end compound of the intended reaction, so the yield of p,p'-biphenol isolated in the first run of reaction for the production of DHBP from TTBP is low. However, if the spent sulfolane is recycled to be used in the second run, the yield of p,p'-biphenol that can be isolated is improved markedly to ensure the production of p,p'-biphenol in substantially stoichiometric amounts and with high yield.

Another advantage of using sulfolane as a reaction solvent is that DHBP and other substances will not adhere to the wall of the reactor, thereby greatly facilitating the handling of the reactor.

We now describe the second aspect of the present invention which provides a process for producing p,p'-biphenol from a mixture of 2,6-di-t-butylphenol and 3,3',5,5'-tetra-t-butyl-4,4'-diphenoquinone or from a mixture of 2,6-di-t-butylphenol, 3,3',5,5'-tetra-t-butyl-4,4'-diphenoquinone and 3,3',5,5'-tetra-t-butyl-4,4'-dihydroxybiphenyl. This process is characterized in that the synthesis of 3,3',5,5'-tetra-t-butyl-4,4'-dihydroxybiphenyl by the redox reaction of 2,6-di-t-butylphenol and 3,3',5,5'-tetra-t-butyl-4,4'-diphenoquinone and the formation of p,p'-biphenol by the dealkylation reaction of 3,3',5,5'-tetra-t-butyl-4,4'-dihydroxybiphenyl are accomplished at one stage in the presence of a solvent and an acid catalyst at a temperature of 120°–280° C.

The starting material used in the second aspect of the present invention for producing p,p'-biphenol is a mixture of 2,6-di-t-butylphenol and 3,3',5,5'-tetra-t-butyl-4,4'-diphenoquinone, or a mixture of 2,6-di-t-butyl-phenol, 3,3',5,5'-tetra-t-butyl-4,4'-diphequinone and 3,3',5,5'-tetra-t-butyl-4,4'-dihydroxybiphenyl.

The weight proportions of 2,6-di-t-butylphenol and 3,3',5,5'-tetra-t-butyl-4,4'-diphenoquinone in the starting material will vary with the total amount of these compounds. Normally, the weight ratio of 3,3',5,5'-tetra-t-butyl-4,4'-diphenoquinone to 2,6-di-t-butyl-phenol ranges from 0.5 to 5, preferably from 1 to 2. It should, however, be noted that the weight ratio of the two compounds is in no way limited to this particular range.

If the weight ratio of 3,3',5,5'-tetra-t-butyl-4,4'-diphenoquinone to 2,6-di-t-butylphenol is less than 1, the former compound will not be effectively used in the redox reaction with the latter. If the weight ratio of 3,3',5,5'-tetra-t-butyl-4,4'-diphenoquinone to 2,6-di-t-butylphenol exceeds 2, the latter compound will not be effectively used in the redox reaction with the former.

It is usually preferable for the content of 2,6-di-t-butylphenol in the starting material to be within the range of 1–50% of the total weight of the starting material which is taken as 100%. If the content of 2,6-di-t-butylphenol is less than 1%, the redox reaction between 2,6-di-t-butylphenol and 3,3', 5,5'-tetra-t-butyl-4,4'-dihydroxybiphenoquinone will contribute only a little to improvement in the yield of p,p'-biphenol. If the content of 2,6-di-t-butylphenol exceeds 50%, it will not be used effectively in the redox reaction wit 3,3',5,5'-tetra-t-butyl 4,4'-dihydroxybiphenoquinone.

It is usually preferable for the content of 3,3',5,5'-tetra-t-butyl-4,4'-diphenoquinone in the starting material to be within the range of 1–50% of the total weight of the starting material. If the content of 3,3',5,5'-tetra-t-butyl-4,4'-diphenoquinone is less than 1%, the redox reaction between 2,6-di-t-butylphenol and, 3,3',5,5'-tetra-t-butyl-4,4'-diphenoquinone will contribute only a little to improvement in the yield of p,p'-biphenol. If the content of 3,3',5,5'-tetra-t-butyl-4,4'-diphenoquinone exceeds 50%, it will not be used effectively in the redox reaction with 2,6-di-butylphenol.

If the weight proportions of 2,6-di-t-butylphenol and 3,3',5,5'-tetra-t-butyl-4,4'-diphenoquinone in the starting material and the contents of these compounds in the starting material are limited to be within the ranges set forth above, the intended redox reaction will take place between these compounds in an efficient manner.

The starting material which satisfies the requirements set forth above can usually be obtained by subjecting 2,6-di-t-butylphenol to oxidative coupling in the presence of oxygen.

As already mentioned, an acid catalyst is used to produce p,p'-biphenol from the starting material which consists of either a mixture of 2,6-di-t-butylphenol and 3,3',5,5'-tetra-t-butyl-4,4'-diphenoquinone or a mixture of 2,6-di-t-butylphenol, 3,3',5,5'-tetra-t-butyl-4,4'-diphenoquinone and 3,3',5,5'-tetra-t-butyl-4,4'-dihydroxybiphenyl. Sulfuric acid or sulfonic acids are preferably used as such acid catalysts. Besides sulfuric acid and sulfonic acid, heteropolyacids may be used as acid catalysts. Useful heteropolyacids include phosphotungstic acid, phosphomolybdic acid and silicomolybdic acid. Other usable acid catalysts include Lewis acids such as aluminum chloride, aluminum isopropoxide and aluminum phenoxide. In certain cases, solid acids may also be used and illustrative solid acids include ion-exchange resins (e.g. Amberlist), mordenite, silica alumina, tetrasilicic mica, activated clay, zeolite, synthetic mica and clay minerals.

The above-listed acid catalysts may be added either before or after the reaction for the synthesis of p,p'-biphenol is started. It should, however, be noted that p,p'-biphenol is not synthesized at all in the absence of any catalyst (see Comparative Example 1 to be described later in this specification).

Solvents are also used in the present invention to produce p,p'-biphenol from the starting material which consists of either a mixture of 2,6-di-t-butylphenol and 3,3'-5,5'-tetra-t-butyl-4,4'-diphenoquinone or a mixture of these compounds with 3,3',5,5'-tetra-t-butyl-4,4'-dihydroxybiphenyl. Specific examples of preferred solvents include phenols, diphenyl ethers, sulfolane, paraffins and gas oil. Illustrative phenols are cresol, t-butylphenol and di-t-butylphenol. Illustrative diphenyl ethers are t-butylphenyl ether and di-t-butyldiphenyl ether. Illustrative paraffins are decane, tridecane and n-paraffin mixtures.

When p,p'-biphenol is to be produced from a mixture of 2,6-di-t-butylphenol and 3,3',5,5'-tetra-t-butyl-4,4'-diphenoquinone or a mixture thereof with TTBP, the reaction temperature is usually set to be within the range of 120°–280° C., preferably 160°–250° C. If this range of reaction temperature is employed, the reaction expressed by scheme (1) will proceed at a faster rate than the reaction expressed by scheme (2), thereby allowing p,p'-biphenol to be produced in high yield.

If the raction temperature is less than 120° C., the redox reaction for producing 3,3',5,5'-tetra-t-butyl-4,4'-dihydroxybiphenyl from 2,6-di-t-butylphenol and 3,3',5,5'-tetra-t-butyl-4,4'-diphenoquinone will not proceed smoothly and instead, isomerization of 2,6-di-t-butylphenol will take place, leading to a lower yield of p,p'-biphenol. If the reaction temperature exceeds 280° C., the operating cost will be increased.

When p,p'-biphenol is to be produced from a mixture of 2,6-di-t-butylphenol and 3,3',5,5'-tetra-t-butyl-4,4'-diphenoquinone or a mixture thereof with 3,3',5,5'-tetra-t-butyl-4,4'-dihydroxybiphenyl, the reaction time will vary greatly with the reaction temperature employed but is normally within the range of from about 1 to about 10 hours.

If a mixture of 2,6-di-t-butylphenol and 3,3',5,5'-tetra-t-butyl-4,4'-diphenoquinone, or a mixture thereof with 3,3',5,5'-tetra-t-butyl-4,4'-dihydroxybiphenyl is treated under the reaction conditions described above concerning catalyst, solvent, temperature and time, the reaction for the synthesis of 3,3',5,5'-tetra-t-butyl-4,4'-dihydroxybiphenyl and that for the dealkylation of this compound will proceed in a balanced and efficient way, thereby allowing p,p'-biphenol to be produced in a satisfactory yield. Stated more specifically, any 3,3',5,5'-tetra-t-butyl-4,4'-diphenoquinone that may be formed on account of excessive oxidation of 3,3',5,5'-tetra-t-butyl 4,4'-dihydroxybiphenyl is reduced with 2,6-di-t-butylphenol to ensure efficient production of 3,3',5,5'-tetra-t-butyl-4,4'-dihydroxybiphenyl therefrom. In addition, the so produced 3,3',5,5'-tetra-t-butyl-4,4'-dihydroxybiphenyl is converted efficiently to p,p'-biphenol by dealkylation.

In producing p,p'-biphenol from a mixture of 2,6-dibutylphenol and 3,3',5,5'-tetra-t-butyl-4,4'-diphenoquinone or a mixture of 2,6-di-butylphenol, 3,3',5,5'-tetra-t-butyl-4,4'-diphenoquinone and 3,3',5,5'-tetra-t-butyl-4,4'-dihydroxybiphenyl in the process of the present invention, the reaction for the synthesis of 3,3',5,5'-tetra-t-butyl-4,4'-dihydroxybiphenyl and the reaction for the dealkylation of 3,3',5,5'-tetra-t-butyl-4,4'-dihydroxybiphenyl are performed at a reaction temperature of 120°–180° C. in the presence of a specified solvent and acid catalyst. Since p,p'-biphenol is directly obtained in one step without separating the 3,3',5,5'-tetra-t-butyl-4,4'-dihydroxybiphenyl that has been formed at the first stage, the present invention offers a simplified process for the production of p,p'-biphenol.

A preferred embodiment of the second aspect of the present invention which is directed to the production of p,p'-biphenol in one step is described hereinafter.

Starting 2,6-di-t-butylphenol is subjected to an oxidative coupling reaction by bringing it into contact with oxygen in the presence of an alkali catalyst, and immediately thereafter, an acid is added to the reaction system, thereby allowing both a redox reaction and a dealkylating reaction to proceed. Alternatively, an inert gas is introduced into the reaction system to make the redox reaction further proceed in the absence of oxygen; thereafter, an acid is added to the reaction system not only to neutralize the alkali catalyst but also to render the reaction system acidic so that 3,3',5,5'-tetra-t-butyl-4,4'-dihydroxybiphenyl is formed by the redox reaction between 3,3',5,5'-tetra-t-butyl-4,4'-diphenoquinone (i.e., a byproduct of the oxidative coupling reaction) and the unreacted 2,6-di-t-butylphenol while at the same time, the 3,3',5,5'-tetra-t-butyl-4,4'dihydroxybiphenyl that has been formed as a result of the oxidative coupling and redox reactions is dealkylated to produce p,p'-biphenol. The steps involved in this process are individually described below in greater detail.

(a) Oxidative coupling reaction of 2,6-di-t-butylphenol:

In the process under discussion, 2,6-di-t-butylphenol is used as the starting material for the production of p,p'-biphenol.

In performing this oxidative coupling reaction of 2,6-di-t-butylphenol [which is hereunder referred to as reaction (a)], an alkali metal hydroxide may be used as an alkali catalyst. It is particularly preferable to use potassium hydroxide in step (a).

When potassium hydroxide is to be used as an alkali catalyst in reaction (a), its addition generally ranges from 0.01 to 1.0 wt %, preferably from 0.03 to 0.5 wt %, of the starting 2,6-di-t-butylphenol. By properly setting the amount of catalyst to be used, the yield of p,p'-biphenol as the final product can be increased.

The alkali catalyst used in reaction (a) may be added as a solid to the reaction system. Alternatively, it may be added as an aqueous solution.

Reaction (a) may be carried out in the presence of a solvent but more preferably, it is performed in the absence of a solvent in order to improve the production rate of p,p'-biphenol. If reaction (a) is to be performed in the presence of a solvent, the latter may be selected from among toluene, xylene, dimethylformamide, t-butyl alcohol, etc.

The temperature for performing reaction (a) is generally within the range of 130°–250° C., preferably in the range of 150°–230° C. The reaction time will vary greatly with other reaction conditions employed but is usually within the range of 0.5–5 hours.

Reaction (a) is allowed to proceed by bringing 2,6-di-t-butylphenol into contact with oxygen. Oxygen may be pure oxygen gas or an oxygen-containing gas such as air. Theoretically, the amount of oxygen to be used in reaction (a) is one quarter of the number of moles of the starting 2,6-di-t-butylphenol. In practice, therefore, oxygen is preferably introduced in an amount which ranges from 80 to 120% of the above-specified theoretical value.

When an oxygen-containing gas is used as an oxygen source in reaction (a), the amount of oxygen spent in the reaction can be easily determined by any standard method such as measuring the concentrations of oxygen in the effluent gas from the reaction system and in the oxygen source. An advantage of using pure oxygen gas as an oxygen source in reaction (a) is that the amount of oxygen spent in the reaction can be determined more easily than when an oxygen-containing gas is used.

Reaction (a) may be performed at either an atmospheric or a superatmospheric pressure. Preferably, it is performed at a superatmospheric pressure in order to improve the yield of p,p'-biphenol.

After reaction (a), an acid may be immediately added to the reaction solution so as to allow the redox and dealkylating reactions to proceed. However, it is more preferable for the purposes of the present invention to introduce an inert gas into the reaction system and perform a reaction in the absence of oxygen that further promotes the redox reaction to e described later in this specification [such a reaction is hereunder sometimes referred to as reaction (b)].

Reaction (b) is performed as follows: when the supply of oxygen or an oxygen-containing gas is completed in reaction (a), an inert gas, typically nitrogen gas, is introduced into the reaction system to purge it of the residual oxygen or oxygen-containing gas and replace it by an inert gas atmosphere. The reaction system is preferably pressurized with an inert gas for carrying out reaction (b). The pressurization of the reaction system is normally effected until the pressure in it builds up to a value between 1 and 5 kg/cm$^2$G in terms of nitrogen pressure.

The temperature for carrying out reaction (b) is normally in the range of 150°–250° C., preferably 180°–230° C. If the reaction temperature is less than 150° C., the reaction rate becomes sometimes too slow to be feasible for practical purposes. If the reaction temperature exceeds 250° C., a decomposition reaction will take place, which is certainly undesirable for the purposes of the present invention.

The period for which reaction (b) is to last will vary with other conditions to be employed but as a guide, the period of 2–6 hours may be selected.

By performing reaction (b) under the conditions described above, 3,3',5,5'-tetra-t-butyl-4,4'-diphenoquinone that has formed as a result of promoted oxidation of 3,3',5,5'-tetra-t-butyl-4,4'-dihydroxybiphenyl enters into a redox reaction with 2,6-di-t-butyl-phenol so as to produce 3,3',5,5'-tetra-t-butyl-4,4'-dihydroxybiphenyl. Therefore, an advantage of including reaction (b) is that the yield of 3,3',5,5'tetra-t-butyl-4,4'-dihydroxybiphenyl as a reaction intermediate is improved over the case where the process does not include reaction (b) and this eventually contributes to an improvement in the yield of p,p'-biphenol as the final product.

(c) Redox reaction and dealkylating reaction under acidic conditions:

In the process of the present invention, a redox reaction and a dealkylating reaction [hereunder collectively referred to as reaction (c)] are performed under acidic conditions, and this is carried out with a predetermined amount of an acid, and optionally a solvent, being added to the system of reaction (a), or to the system of reaction (b) if the latter is included in the process. An acid is added to either reaction system in an amount that is more than necessary to neutralize the alkali catalyst added to the system of reaction (a) to perform the oxidative coupling reaction of 2,6-di-t-butylphenol. In short, reaction (c) is performed under the following general conditions: the alkali catalyst used in reaction (a) and/or (b) is neutralized to form a salt with a freshly supplied acid without being separated from the system of either reaction, and an excess acid is further added to the system of reaction (c) so as to render it acidic, with the added acid being used as a catalyst for reaction (c).

In reaction (c), the acid is added to the reaction solution obtained in reaction (a), or to the reaction solution obtained in reaction (b) if it is included, in such an amount that the pH of the reaction system will lie within the range of 0–3, preferably 0–2.

There is no particular limitation on the amount of solvent to be used in reaction (c) and it is generally desired for the solvent to be added to reaction solution (a) or (b) in an amount of 0.1–20 parts by weight, preferably 0.5–10 parts by weight.

When the reaction solution is heated, with stirring, to a temperature between 170° and 300° C., preferably between 180° and 250° C., and if the heating is continued for a period that normally lasts for 2–6 hours,(i) the reaction for producing 3,3',5,5'-tetra-t-butyl-4,4'-dihydroxybiphenyl by the redox reaction between 3,3',5,5'-tetra-t-butyl-4,4'-diphenoquinone (i.e. a by-product of the oxidative coupling reaction of 2,6-di-t-butylphenol) and the unreacted 2,6-di-t-butylphenol and ii) the reaction for producing p,p'-biphenol by dealkylation of the 3,3',5,5'-tetra-t-butyl-4,4'-dihydroxybiphenyl that has formed in such reactions as the oxidative coupling reaction (a) and the redox reaction (b) are allowed to proceed in one step. If the temperature for performing reaction (a) exceeds 300° C., a condition favorable for the decomposition of p,p'-biphenol produced will result. If the reaction temperature is less than 170° C., it will take an unduly long time for the 3,3',5,5'-tetra-t-butyl-4,4'-dihydroxybiphenyl to be dealkylated to p,p'-biphenol.

Acids that can be used in performing reaction (c) include sulfuric acid, hydrochloric acid, acetic acid, benzenesulfonic acids, silica/alumina, activated clay, etc. Among these examples, sulfuric acid and p-toluenesulfonic acid are preferred since they are readily available as industrial materials and need not be separated as the catalyst from the product p,p'-biphenol. If economy is also taken into consideration, sulfuric acid is more preferred.

Solvents that can be employed in reaction (c) include benzofuran, diphenyl ether, diphenyl, saturated hydrocarbons, sulfolane, phenol, alkylphenols, etc.

The temperature of the reaction system is maintained within the range set forth above until the generation of isobutene accompanying the dealkylation reaction is substantially terminated, whereupon a reaction solution containing p,p'-biphenol is obtained by reaction (c). This reaction solution is then cooled to precipitate p,p'-biphenol, which is separated by filtration. The resulting crude p,p'-biphenol is washed with a small amount of solvent such as toluene, and subsequently dried to yield a white crystal of p,p'-biphenol which has been purified to at least 99%.

The isobutene which has evolved as a result of dealkylation of 3,3',5,5'-tetra-t-butyl-4,4'-dihydroxybiphenyl in reaction (c) is separated from the other reaction products with a reflux condenser and discharged from the reaction system. The discharged isobutene is recovered in gaseous form and recycled for another use.

After reaction (c) is performed in the manner described above, an aqueous alkaline solution may be added to the reaction system so as to neutralize the acid used as a catalyst in reaction (c) and to have a salt of said catalyst precipitated as a crystal. The precipitating crystal is separated while hot from p,p'-biphenol by filtration and the resulting filtrate is cooled to recover p,p'-biphenol as a crystal. The major advantage of this practice lies in the fact the salt formed by the reaction of neutralization of the catalyst is not incorporated in p,p'-biphenol obtained as the final product.

The process of the present invention offers the following advantage. (1) In producing p,p'-biphenol from 2,6-di-t-butylphenol, neither the 3,3',5,5'-tetra-t-butyl-4,4'-diphydroxybiphenyl nor 3,3',5,5'-tetra-t-butyl-4,4'-diphenoquinone that have been formed by the oxidative coupling reaction of 2,6-di-t-butylphenol is separated from the starting 2,6-di-t-butylphenol and instead an acid is added to the reaction system so that not only is the alkali catalyst in the reaction system neutralized but also the latter is rendered acidic to provide a condition favorable for a redox reaction to occur between 2,6-di-t-butylphenol and 3,3',5,5'-tetra-t-butyl-4,4'-diphenoquine, thereby producing 3,3',5,5'-tetra-t-butyl-4,4'-diphydroxybiphenyl. Simultaneously with this redox reaction, a reaction also occurs for dealkylating 3,3',5,5'-tetra-t-butyl-4,4'-dihydroxybiphenyl.

Therefore, in accordance with the process of the present invention, p,p'-biphenol can be produced continuously without separating the reaction intermediates or catalyst, and this contributes to the purpose of greatly simplifying the overall production process.

If desired, reaction (b) may be carried out after reaction (a), or the oxidative coupling reaction of 2,6-di-t-butylphenol has been affected, and this offers the advantage of further improving the yield of p,p'-biphenol as compared with the case where reaction (b) is not included. (2) The process eliminates the need to separate the intermediate product 3,3',5,5'-tetra-t-butyl-4,4'-dihydroxybiphenyl from the catalyst, and cumbersome procedures that are associated with its separation including isolation and washing with a solvent, as well as recrystallization become entirely unnecessary, thus leading to simplification of the steps involved in the production of p,p'-biphenol. Furthermore, the process of the present invention obviates the need to install complicated facilitates for treating the effluent water, thereby contributing to the purpose of streamlining the overall process of p,p'-biphenol production. (3) Isobutene which is formed together with p,p'-biphenol in reaction (c) can be recovered as a gas which finds effective use in other applications.

The following examples are provided for the purpose of further illustrating the present invention but should in no way be taken as limiting.

EXAMPLE 1

A 300-ml reaction flask equipped with a gas withdrawing port was charged with 100 g of TTBP as the starting material, 100 g of tridecane as a solvent and 0.5 g of p-toluenesulfonic acid as a catalyst. The contents were subjected to debutylation at 230° C. for 130 minutes.

Thereafter, the temperature in the reaction flask was lowered to 80° C. so as to precipitate the crystal of p,p'-biphenol. The precipitating p,p'-bephenol crystal was separated from the reaction solution by filtration and washed with 100 ml of toluene to obtain a pure crystal of p,p'-biphenol in an amount of 44.3 g. The purity and yield of this product were 99.6% and 97.6%, respectively.

Isobutylene was obtained from the starting TTBP in an amount of 54.4 g. This is equivalent to saying that conversion of the starting TTBP was 99.5%. The isobutylene obtained had a purity of 100%.

COMPARATIVE EXAMPLE 1

The procedures of Example 1 were repeated except that the reaction was performed at 230° C. for 85 minutes with 100 g of biphenyl being used as a solvent. As a result, p,p'-biphenol was produced in an amount of 38.8 g (yield, 84.4%) with a purity of 98.6%.

Isobutylene was obtained from TTBP in an amount of 50.1 g. This yield of isobutylene corresponds to 91.7% conversion of the starting TTBP.

EXAMPLE 2

The procedures of Example 1 were repeated except that the reaction was performed at 230° C. for 50 minutes with 100 g of Lucant ® HC-20 whose iodine value was not more than 1.0 being used as a solvent. As a result, p,p'-biphenol was obtained in an amount of 44.0 g (yield, 97.0%) with a purity of 99.2%.

Isobutylene was also obtained as a by-product of the reaction of TTBP. This yield of isobutylene corresponds to 94.0% conversion of the starting TTBP.

COMPARATIVE EXAMPLE 2

The procedures of Example 1 were repeated except that the reaction was performed at 230° C. for 100 minutes with 100 g of diphenyl ether being used as a solvent. As a result, p,p'-biphenol was produced in an amount of 37.4 g (yield, 82.3%) with a purity of 99.2%.

Isobutylene was obtained as a by-product of the reaction of TTBP. This yield of isobutylene corresponds to 89.2% conversion of the starting TTBP.

EXAMPLE 3

A 300-ml reaction flask furnished with a gas withdrawing port was charged with 100 g of TTBP as the starting material, 100 g of sulfolane as a solvent and 0.5 g of p-toluenesulfonic acid (hereinafter sometimes abbreviated as p-TSOH) as a catalyst. Reaction was initiated by placing the flask in an oil bath that had been heated to 230° C. The quantity of isobutene produced during the reaction was measured with a gas meter installed on the gas withdrawing port.

After the reaction for the formation of p,p'-biphenyl was continued at 230° C. for 1.5 hours, the temperature of the oil bath was lowered to 150° C. so as to precipitate DHBP.

By suction filtration, the contents of the reactor containing the DHBP precipitate were separated into a solid portion (which contained DHBP) and a liquid portion which was the reaction solution. The solid portion which contained DHBP was washed with toluene to obtain a DHBP crystal. This crystal had a purity of 99.7% and was found to have been isolated in a yield of 60%.

Isobutene was generated in an amount of 51.5 g as a result of the reaction and this is equivalent to the yield of 94.3% on the basis of the starting TTBP.

EXAMPLE 4

The procedures of Example 3 were repeated except that 100 g of starting TTBP was charged into the reaction system with 123.9 g of the reaction solution obtained in Example 3 being used as a solvent instead of supplying an additional amount of sulfolane as a solvent. The DHBP obtained had a purity of 99.5% and it was found to have been isolated in a yield of 98.0%.

Isobutene was generated in an amount of 54.6 g and this is equivalent to the yield of 100% on the basis of the starting TTBP.

EXAMPLE 5

A 50-ml reaction flask furnished with a gas withdrawing port was charged with 10 g of crude (85.6%) TTBP, 10 g of sulfolane as a solvent and 0.16 g of sulfuric acid as a catalyst. Reaction was initiated by placing the reaction flask in an oil bath that had been heated to 230° C. After 2hr reaction, the temperature of the oil bath was lowered to 40° C. so as to precipitate DHBP. The precipitating DHBP crystal was separated from the reaction solution by suction filtration and washed with toluene to obtain the DHBP crystal. The purity and yield of this product were 99.8% and 42.3%, respectively.

EXAMPLE 6

The procedures of Example 5 were repeated except that 10 g of crude (85.6%) TTBP and 0.08 g of sulfuric acid (catalyst) were additionally supplied to 13.6 g of the reaction solution obtained in Example 5. The DHBP obtained had a purity of 99.7% and was found to have been isolated in a yield of 102%.

EXAMPLE 7

The procedures of Example 6 were repeated except that 10 g of crude (85.6%) TTBP and 0.08 g of sulfuric acid (catalyst) were additionally supplied to 14.5 g of the reaction solution obtained in Example 6. The DHBP obtained had a purity of 99.5% and was found to have been isolated in a yield of 107%.

EXAMPLE 8

A starting material which was a mixture of 3,3',5,5'-tetra-t-butyl-4,4'-diphenoquinone (1.0 g) and 2,6-di-t-butylphenol (1.0 g) was subjected to reaction at 180° C. for 1 hour in a nitrogen gas atmosphere using 10 ml of phenol as a solvent and 0.05 g of sulfuric acid as a catalyst. p,p'-biphenol was produced in an amount of 0.49 g (yield, 54.0%).

EXAMPLE 9

A starting material which was a mixture of 3,3',5,5'-tetra-t-butyl-4,4'-diphenoquinone (1.0 g) and 2,6-di-t-butylphenol (1.0 g) was subjected to reaction at 180° C. for 1 hour in a nigrogen gas atmosphere using 10 ml of phenol as a solvent. Thereafter, 0.03 g of sulfuric acid was added to the reaction solution as a catalyst and the reaction was continued for an additional 1 hour at 180° C. in a nitrogen gas atmosphere. As a result, p,p'-biphenol was obtained in an amount of 0.56 g (yield, 62.5%).

EXAMPLE 10

A starting material which was a mixture of 3,3',5,5'-tetra-t-butyl-4,4'-diphenoquinone (0.46 g), 2,6-di-t-butylphenol (0.34 g) and 3,3',5,5'-tetra-t-butyl-4,4'-dihydroxybiphenyl (8.56 g) was subjected to reaction at 180° C. for 6 hours in a nitrogen gas atmosphere using 20 g of phenol as a solvent and 0.04 g of sulfuric acid as a catalyst. As a result, p,p'-biphenol was obtained in an amount of 3.35 g (yield, 79.9%).

COMPARATIVE EXAMPLE 3

A starting material which was a mixture of 3,3',5,5'-tetra-t-butyl-4,4'-diphenoquinone (0.5 g), 2,6-di-t-butylphenol (1.5 g) and 3,3', 5,5'-tetra-t-butyl-4,4'-dihydroxybiphenyl (8.0 g) was subjected to reaction at 190° C. for 2 hours in a nitrogen gas atmosphere using 20 g of phenol as a solvent in the absence of a catalyst. As a result, 3,3'-5,5'-tetra-t-butyl-4,4'-diphenoquinone, 2,6-di-t-butylphenol and 3,3',5,5'-tetra-t-butyl-4,4'-dihydroxybiphenyl were obtained in respective amounts of 0.13 g, 1.13 g and 8.74 g.

EXAMPLE 11

A starting material which was a mixture of 3,3', 5,5'-tetra-t-butyl-4,4'-diphenoquinone (0.95 g), 2,6-di-t-butylphenol (0.75 g) and 3,3',5,5'-tetra-t-butyl-4,4'-dihydryoxybiphenyl (21.7 g) was subjected to reaction at 240° C. for 2 hours in a nitrogen gas atmosphere using 25 g of gas oil as a solvent and 0.6 g of sulfuric acid as a catalyst. As a result, p,p'-biphenol was obtained in an amount of 9.96 g considering the redox reaction that occurred, the yield of p,p'-biphenol was 94.6%, which is equivalent to the yield of 101% on the sole basis of 3,3',5,5'-tetra-t-butyl-4,4'-dihydroxybiphenyl in the starting material

EXAMPLE 12

A 500-ml autoclave equipped with a stirrer, a thermometer, a gas blowing pipe and a reflux condenser was charged with 150 g (0.73 moles) of 2,6-di-butylphenol and 0.3 g (1.34 mmol) of a 25% aqueous solution of potassium hydroxide and the charged solution was heated to 185° C. Air was blown at a rate of 0.3 L/min into the autoclave to a pressure of 5 kg/cm$^2$G and a substantially stoichiometric amount (0.17 moles) of oxygen was reacted with 2,6-di-t-butylphenol for 3 hours. The amount of oxygen that had been spent in the reaction was determined by calculation of the concentration of oxygen in the blown air and that of oxygen in the effluent gas from the autoclave.

In the next step, nitrogen gas was supplied into the reaction system to replace the air atmosphere in it by a nitrogen gas atmosphere. The pressure in the reaction system was maintained at 2 kg/cm$^2$G in terms of nitrogen pressure and the redox reaction between 2,6-di-t-butylphenol and 3,3',5,5'-tetra-t-butyl-4,4'-diphenoquinone was performed at 190° C. 2 hours to obtain reaction solution (1).

A portion (10.0 g) of this reaction solution was used in the subsequent process. Phenol (20 g) and sulfuric acid (0.04 g) were added to 10.0 g of reaction solution (1) not only for neutralizing the base in the reaction system but also to render the reaction solution acidic (pH, 1). Thereafter, the following two reactions were performed in one step at 180° C. over a period of 6 hours: a redox reaction in which the unreacted 2,6-di-t-butylphenol and 3,3',5,5'-tetra-t-butyl-4,4'-diphenoquinone were reacted to produce 3,3',5,5'-tetra-t-butyl-4,4'-dihydroxybiphenyl; and a reaction in which 3,3',5,5'-tetra-t-butyl-4,4'-dihydroxybiphenyl was dealkylated into p,p'-biphenol.

After completion of these reactions, the reaction mixture was cooled to 60° C. and then filtered to separate the mother liquor (I) from a crude crystal of p,p'-biphenol, The resulting crystal was washed with toluene and dried to obtain purified p,p'-biphenol.

This p,p'-biphenol weighed 3.35 g and its yield was 86.3% based on 3,3',5,5'-tetra-t-butyl-4,4'-dihydroxybiphenyl. The overall yield of p,p'-biphenol was 73.8% and it was no less pure than 99%.

EXAMPLE 13

Phenol (20.7 g) and sulfuric acid (0.08 g) were added to 10.0 g of the reaction solution (1) obtained in Example 12, so as to neutralize the alkali base catalyst in the reaction solution (1) and to render it acidic (pH, 1).

Thereafter, the following two reactions were performed in one step by heating the reaction solution (1) at 180° C. over a period of 6 hours: a redox reaction in which the unreacted 2,6-di-t-butylphenol and 3,3',5,5'-tetra-t-butyl-4,4'-diphenoquinone were reacted to produce 3,3',5,5'-tetra-t-butyl-4,4'-dihydroxybiphenyl; and a reaction in which 3,3',5,5'-tetra-t-butyl-4,4'-dihydroxybiphenyl was dealkylated into p,p'-biphenol.

After completion of these reactions the reaction mixture was cooled to 60° C. and filtered to separate the mother liquor from a crude crystal of p,p'-biphenol. The resulting crystal was washed with toluene and dried to obtain purified p,p'-biphenol.

This p,p'-biphenol weighed 3.38 g and its yield was 87.1% based on 3,3',5,5'-tetra-t-butyl-4,4'-dihydroxybiphenyl. The overall yield of the purified p,p'-biphenol was 74.5% and it was no less pure than 99%.

EXAMPLE 14

The procedures of Example 12 were repeated except that 10.0 g of reaction solution (1) obtained in Example 12, 0.1 g of phenol (solvent) and 0.04 g of sulfuric acid (catalyst) were added to the whole portion of mother liquor (I) obtained in Example 12 and that reaction was performed at 185° C. for 3 hours to produce p,p'-biphenol.

The crude p,p'-biphenol produced by dealkylating 3,3',5,5'-tetra-t-butyl-4,4'-dihydroxybiphenyl weighted 3.53 g and its yield was 91% based on 3,3',5,5'-tetra-t-butyl-4,4'-dihydroxybiphenyl in the charged reaction solution. The overall yield of the pure p,p'-biphenol obtained by purifying the crude product was 77.8% and it was no less pure than 99%.

EXAMPLE 15

The procedures of Example 13 were repeated except (that 20.0 g of tridecane (solvent) and 0.05 g of ptoluenesulfonic acid (catalyst) were added to 10.0 g of reaction solution (1) obtained in Example 12 so as to neutralize the alkali catalyst base in reaction solution (1) and to render it acidic (pH, 1).

The product p,p'-biphenol weighed 3.50 g and its yield was 90.3% based on 3,3',5,5'-tetra-t-butyl-4,4'dihydroxybiphenyl. The overall yield of the purified p,p'-biphenol was 77.2% and it was no less pure than 99%.

EXAMPLE 16

A 500-ml autoclave of the same type as what was used in Example 12 was charged with 100 g (0.49 moles) of 2,6-di-t-butylphenol and 1.0 g (8.93 mmol) of a 50% aqueous solution of potassium hydroxide and the charged solution was heated to 200° C. When pure oxygen was blown into the autoclave to a pressure of 7 kg/cm$^2$G, the reaction temperature rose to 215° C. When the pressure in the autoclave dropped to 4 kg/cm$^2$G, pure oxygen was additionally supplied into the autoclave to raise the pressure to 7 kg/cm$^2$G. With two more supplies of additional oxygen, a substantially stoichiometric amount (0.12 moles) of oxygen was reacted with 2,6-di-t-butylphenol for 1 hour to obtain reaction solution (2).

A portion (10.0 g) of this reaction solution (2) was used in the subsequent process. Sulfolane (10 g) and sulfuric acid (0.10 g) were added to 10.0 g of the reaction solution (2) not only for neutralizing the base in the reaction system but also to render the reaction solution (2) acidic (pH, 1).

Thereafter, the following two reactions were performed in one step at 230° C. over a period of 2 hours: a redox reaction in which the untreated 2,6-di-butylphenol and 3,3',5,5'-tetra-t-butyl-4,4'-diphenoquinone were reacted to produce 3,3',5,5'-tetra-t-butyl-4,4'-dihydroxybiphenyl; and a reaction in which 3,3',5,5'-tetra-t-butyl-4,4'-dihydroxybiphenyl was dealkylated into p,p'-biphenol.

After completion of these reactions, the reaction mixture was cooled to 60° C. and then filtered to separate the mother liquor (II) from a crude crystal of p,p'-biphenol. The resulting crystal was washed with toluene and dried to obtain purified p,p'-biphenol.

This p,p'-biphenol weighed 2.45 g and its yield was 61.2% based on 3,3',5,5'-tetra-t-butyl-4,4'-dihydroxybiphenyl. The overall yield of the purified p,p'-biphenol was 54.0% and it was no less pure than 99%.

EXAMPLE 17

The procedures of Example 16 were repeated except that 10.0 g of reaction solution (2) obtained in Example 16, 0.5 g of sulfolane (solvent) and 0.10 g of sulfuric acid (catalyst) were added to the whole portion of mother liquor (II) obtained in Example 16, and that reaction was performed at 230° C. for 2 hours to produce p,p'-biphenol.

The crude p,p'-biphenol produced by dealkylating 3,3',5,5'-tetra-t-butyl-4,4'-dihydroxybiphenyl weighed 3.79 g and its yield was 95% based on 3,3',5,5'-tetra-t-butyl-4,4'-dihydroxybiphenyl in the charged reaction solution. The overall yield the pure p,p'-biphenol obtained by purifying the crude product was 83.5% and it was no less pure than 99%.

What is claimed is:

1. A process for producing p,p'-biphenol by the dealkylation reaction of 3,3',5,5''-tetra-t-butyl-4,4'-dihydroxybiphenyl, said reaction being carried out in the presence of at least one acid catalyst selected from the group consisting of sulfuric acid, a sulfonic acid, a heteropoly acid, a Lewis acid and a solid acid, using a solvent selected from the group consisting of a saturated hydrocarbon having a boiling point of 190° C. or above, an alicyclic hydrocarbon having a boiling point of 190° C. or above, a hydrocarbon with an iodine value of no more than 1, sulfonane, and a mixture of these solvents, at a temperature of from 150° to 300° C. when each of said solvents except for sulfolane is used, and at a temperature from 150° to 285° C. when sulfolane is used.

2. In a process for producing p,p'-biphenol from a mixture of 2,6-di-t-butylphenol and 3,3',5,5'-tetra-t-butyl-4,4'-diphenoquinone or from a mixture of 2,6-di-t-butylphenol, 3,3',5,5'-tetra-t-butyl-4,4'-diphenoquinone and 3,3',5,5'-tetra-t-butyl-4,4'-di-hydroxybiphenyl, the improvement wherein the synthesis of 3,3',5,5'-tetra-t-butyl-4,4'-dihydroxybiphenyl by the redox reaction between 2,6-di-t-butylphenol and 3,3',5,5'-tetra-t-butyl-4,4'-diphenoquinone, wherein the weight ratio of the 3,3',5,5'-diphenoquinone to 2,6-di-t-butyl-phenol in the starting material ranges from 0.5 to 5 and the production of p,p'-biphenol in the dealkylation reaction of 3,3',5,5'-tetra-t-butyl- 4,4'-dihydroxybiphenyl are performed at one stage in the presence of both at least one acid catalyst selected from the group consisting of sulfuric acid, a sulfonic acid, a heteropoly acid, a Lewis acid and a solid acid, and a solvent selected from the group consisting of a saturated hydrocarbon having a boiling point of 190° C. or above, an alicyclic hydrocarbon having a boiling point of 190° C. or above a hydrocarbon with an iodine value of no more than 1, sulfonane, and a mixture of those solvents, at a temperature of 120°–280° C.

3. A process according to claim 2, wherein the reaction for the synthesis of 3,3',5,5'-tetra-t-butyl-4,4'-dihydroxybiphenyl is carried out using as a solvent at least one member selected from the group consisting of phenols, diphenyl ethers, sulfolane, paraffins and gas oil.

4. A process for producing p,p'-biphenol comprising the steps of
  oxidatively coupling 2,6-di-t-butylphenol by bringing it into contact with oxygen wherein the amount of oxygen is 80 to 120% of the theoretical value, which is one quarter of the number of moles of the starting 2,6-di-t-butylphenol, in the presence of an alkali metal hydroxide catalyst at a temperature of 130° to 250° C.;
  adding at least one acid selected from the group consisting of sulfuric acid, hydrochloric acid, acetic acid, benzenesulfonic acid, silica/alumina and activated clay to the reaction system for neutralizing said alkali catalyst, as well as to render the reaction system acidic, so that 3,3',5,5'-tetra-t-butyl-4,4'-dihydroxybiphenyl is produced by the redox reaction between the 3,3',5,5'-tetra-t-butyl-4,4'-diphenoquinone, which has formed as a by-product of the oxidative coupling reaction and the unreacted 2,6-di-t-butylphenol, while at the same time, the 3,3',5,5'-tetra-t-butyl-4,4'-dihydroxybiphenyl, which has formed as a result of the oxidative coupling reaction and the redox reaction, is dealkylated to produce p,p'-biphenol, at a temperature of 170 to 300° C.

5. A Process for producing p,p'-biphenol comprising the steps of:
  oxidatively coupling 2,6-di-t-butylphenol by bringing it into contact with oxygen wherein the amount of oxygen is 80 to 120% of the theoretical value, which is one quarter of the number of moles of the starting 2,6-di-t-butylphenol, in the presence of an alkali metal hydroxide catalyst at a temperature of 130° to 250° C.;
  introducing an inert gas into the reaction system so that the redox reaction is allowed to proceed in the absence of oxygen at a temperature of 150° to 250° C.; then
  adding at least one acid selected from the group consisting of sulfuric acid, hydrochloric acid, acetic acid, benzeneaulfonic acid, silica/alumina and activated clay to the reaction system for neutralizing said alkali catalyst as well as to render the reaction system acidic so that 3,3',5,5'-tetra-t-butyl-4,4'-dihydroxybiphenyl is produced by the redox reaction between the 3,3',5,5'-tetra-t-butyl-4,4'-diphenoquinone, which has formed as a by-product of the oxidative coupling reaction and the unreacted 2,6-di-butylp,henol, while at the same time, the 3,3',5,5'-tetra-t-butyl-4,4'-dihydroxybiphenyl, which has formed as a result of the oxidative coupling reaction and the redox reaction, is dealkylated to produce p,p'-biphenol, at a temperature of 170° to 300° C.

* * * * *

UNITED STATES PATENT AND TRADEMARK OFFICE
CERTIFICATE OF CORRECTION

PATENT NO. : 4,891,453

DATED : January 2, 1990

INVENTOR(S) : Michio Tanaka, et al

It is certified that error appears in the above-identified patent and that said Letters Patent is hereby corrected as shown below:

IN THE CLAIMS:

Claim 1, line 51, column 18, change "sulfonane" to --sulfolane--.

Claim 2, line 10, column 19, change "sulfonane" to --sulfolane--.

Claim 5, line 30, column 20, change "2,6-di-butylp,henol" to --2,6-di-butylphenol--

Signed and Sealed this

Ninth Day of April, 1991

Attest:

HARRY F. MANBECK, JR.

*Attesting Officer*     *Commissioner of Patents and Trademarks*